(12) United States Patent
Hsu et al.

(10) Patent No.: US 11,883,665 B2
(45) Date of Patent: Jan. 30, 2024

(54) NEUROSTIMULATORS AND RELATED SYSTEMS AND METHODS

(71) Applicant: Unity HA LLC, Effingham, IL (US)

(72) Inventors: William Hsu, Santa Clara, CA (US); Anthony Caparso, Avon, OH (US); Thomas Luhrs, Pacifica, CA (US); Ian G. Welsford, Concord, CA (US); Mark Van Kerkwyk, Gilroy, CA (US); Vimal Ganesan, Mountain View, CA (US)

(73) Assignee: UNITY HA LLC, Effingham, IL (US)

( * ) Notice: Subject to any disclaimer, the term of this patent is extended or adjusted under 35 U.S.C. 154(b) by 160 days.

(21) Appl. No.: 17/183,293

(22) Filed: Feb. 23, 2021

(65) Prior Publication Data
US 2021/0275814 A1 Sep. 9, 2021

Related U.S. Application Data

(63) Continuation of application No. 16/466,396, filed as application No. PCT/US2017/064655 on Dec. 5, 2017, now abandoned.
(Continued)

(51) Int. Cl.
| | |
|---|---|
| *A61N 1/36* | (2006.01) |
| *A61N 1/05* | (2006.01) |
| *A61N 1/375* | (2006.01) |
| *A61N 1/372* | (2006.01) |
| *A61N 1/378* | (2006.01) |

(52) U.S. Cl.
CPC ....... *A61N 1/36075* (2013.01); *A61N 1/0546* (2013.01); *A61N 1/372* (2013.01); *A61N 1/3787* (2013.01); *A61N 1/37217* (2013.01); *A61N 1/37518* (2017.08)

(58) Field of Classification Search
CPC .............. A61N 1/36075; A61N 1/0546; A61N 1/37518; A61N 1/3787; A61N 1/0526; A61N 1/0531; A61N 1/0563; A61N 1/0539; A61N 1/0551
See application file for complete search history.

(56) References Cited

U.S. PATENT DOCUMENTS

| | | | |
|---|---|---|---|
| 8,135,477 B2 * | 3/2012 | Fattouh | A61N 1/0551 607/117 |
| 8,781,574 B2 | 7/2014 | Pless et al. | |

(Continued)

OTHER PUBLICATIONS

PCT International Search Report and Written Opinion for corresponding International Application Serial No. PCT/US2017/064655, dated Feb. 23, 2018, 1-13 pages, United States.

*Primary Examiner* — Brian T Gedeon
(74) *Attorney, Agent, or Firm* — Stinson LLP

(57) ABSTRACT

One aspect of the present disclosure relates to a system for treating a medical condition in a patient. The system can include a neurostimulator that is in electrical communication with a remote transducer. The neurostimulator can be sized and dimensioned for injection or insertion into a pterygopalatine fossa (PPF) of a patient. The remote transducer, when activated and brought into close proximity to the patient's head, can cause the neurostimulator to deliver an electrical signal to a target neural structure located within the PPF to treat the medical condition.

9 Claims, 8 Drawing Sheets

Related U.S. Application Data

(60) Provisional application No. 62/430,076, filed on Dec. 5, 2016.

(56) References Cited

U.S. PATENT DOCUMENTS

| | | |
|---|---|---|
| 9,162,073 B2 | 10/2015 | Rezai et al. |
| 2006/0235484 A1 | 10/2006 | Jaax et al. |
| 2010/0185258 A1 | 7/2010 | Papay |
| 2011/0125215 A1* | 5/2011 | Goetz ................ A61N 1/36017 607/45 |
| 2011/0172739 A1 | 7/2011 | Mann et al. |
| 2012/0290057 A1* | 11/2012 | Boling .................. A61B 17/24 607/116 |
| 2013/0066393 A1 | 3/2013 | Gross et al. |
| 2013/0116745 A1* | 5/2013 | Fletcher ............. A61N 1/36075 607/46 |
| 2013/0345716 A1* | 12/2013 | Powell ............... A61B 17/3403 606/129 |
| 2015/0180271 A1* | 6/2015 | Angara .................. H02J 50/12 320/108 |
| 2015/0341785 A1* | 11/2015 | Young ................ A61N 1/37252 607/60 |
| 2016/0001079 A1 | 7/2016 | Fletcher et al. |
| 2016/0331956 A1 | 11/2016 | Yakovlev et al. |
| 2016/0346530 A1* | 12/2016 | Jeffery ................ A61N 1/0492 |

* cited by examiner

NEUROSTIMULATORS AND RELATED SYSTEMS AND METHODS

RELATED APPLICATIONS

The present application claims priority to U.S. Provisional Application No. 62/430,076, entitled "Neurostimulators and Related Systems and Methods," filed on Dec. 5, 2016, the entirety of which is incorporated by reference herein.

TECHNICAL FIELD

The present disclosure relates generally to delivery of energy impulses (and/or energy fields) to bodily tissues for therapeutic purposes and, more particularly, to the use of electrical stimulation of the sphenopalatine ganglion (SPG) and other sensory and autonomic nerves for treating disorders in a patient, such as headache or pain.

BACKGROUND

The sphenopalatine ganglion (SPG) (also known as the pterygopalatine ganglion, ganglion pterygopalatinum, Meckel's ganglion, and nasal ganglion) is a nerve ganglion found in the pterygopalatine (sphenopalatine) fossa, close to the sphenopalatine foramen. The SPG has been a clinical target to treat severe headaches since Sluder first described the application of cocaine or alcohol to the vicinity of the SPG, by swabbing through the nostril to the nasopharyngeal mucosa posterior to the middle turbinate. Unfortunately, the SPG swabbing produces only a brief respite from pain, whether by using a cotton swab as originally described by Sluter, or by means of a topical administration device. In addition, injection into the pterygopalatine fossa (PPF) is difficult to perform reliably due to considerable anatomical variability of the patients, with damage to the maxillary artery that lies next to the SPG being not uncommon. Furthermore, the nasal mucosa may slough during needle insertion. Nevertheless, such pharmacological blockade of the SPG has been claimed to be an effective treatment for headaches, asthma, angina, hiccups, epilepsy, glaucoma, neck pain, vascular spasms, facial neuralgias, blindness, low back pain, sciatica, ear ache, menstrual pain, temporomandibular joint dysfunction, and hyperthyroidism.

More recently, anesthetic has been injected into the PPF using modifications of the Sluder methods and devices. Nevertheless, the internal maxillary artery may be at risk no matter where the PPF is punctured.

In addition to the ganglion blockade using anesthetics as described above, ablation (percutaneous radiofrequency, gamma knife, and surgical gangionectomy) and electrical nerve stimulation have been used to treat pain (especially cluster headaches) originating in, or emanating from, the SPG. The objective of the ablation is to irreversibly damage the SPG to such an extent that it cannot generate the nerve signals that cause pain. This is not a preferred method because ablation would destroy useful neurophysiological functions of the SPG, notwithstanding the pain that the SPG may cause.

In contrast to ablation, the objective of electrical nerve stimulation is to reversibly damage or otherwise inhibit or block activity the SPG. A significant advantage of electrical stimulation over ablation is that it is a reversible procedure. In that regard, SPG neurostimulation resembles the stimulation of other nerves for the treatment of primary headache disorders.

SUMMARY

The present disclosure relates generally to delivery of energy impulses (and/or energy fields) to bodily tissues for therapeutic purposes and, more particularly, to the use of electrical stimulation of the sphenopalatine ganglion (SPG) and other sensory and autonomic nerves for treating disorders in a patient, such as headache or pain.

One aspect of the present disclosure relates to a system for treating a medical condition in a patient. The system can comprise a sheath having an inner lumen with a proximal end and a distal end. The system can also include a neurostimulator sized and dimensioned for injection or insertion into the pterygopalatine fossa (PPF) of a patient. The neurostimulator can comprise a plurality of expandable electrical leads each comprising a plurality of independently selectable electrical contacts. The plurality of expandable electrical leads are disposed within the sheath's inner lumen in a non-deployed configuration and splay radially outward from the distal end of the sheath's inner lumen in a deployed configuration. The system can further include a remote transducer that is in electrical communication with the neurostimulator. When activated and brought into close proximity to the patient's head, the remote transducer causes the neurostimulator to deliver an electrical signal to a target neural structure located within the PPF to treat the medical condition.

Another aspect of the present disclosure relates to a method for treating a medical condition in a patient. The method can comprise inserting or injecting a sheath into a PPF of the patient. The sheath can have an inner lumen with a proximal end and a distal end. A neurostimulator is disposed within the sheath and comprises a plurality of expandable electrical leads each comprising a plurality of independently selectable electrical contacts. The method can further include advancing the sheath to a target neural structure in the PPF. The plurality of expandable electrical leads can be deployed to splay outwards from the sheath and fully or partially encapsulate the target neural structure. The method can further comprise activating one or more of the plurality of independently selectable electrical contacts to deliver a therapeutic electrical signal to the target neural structure to treat the medical condition.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
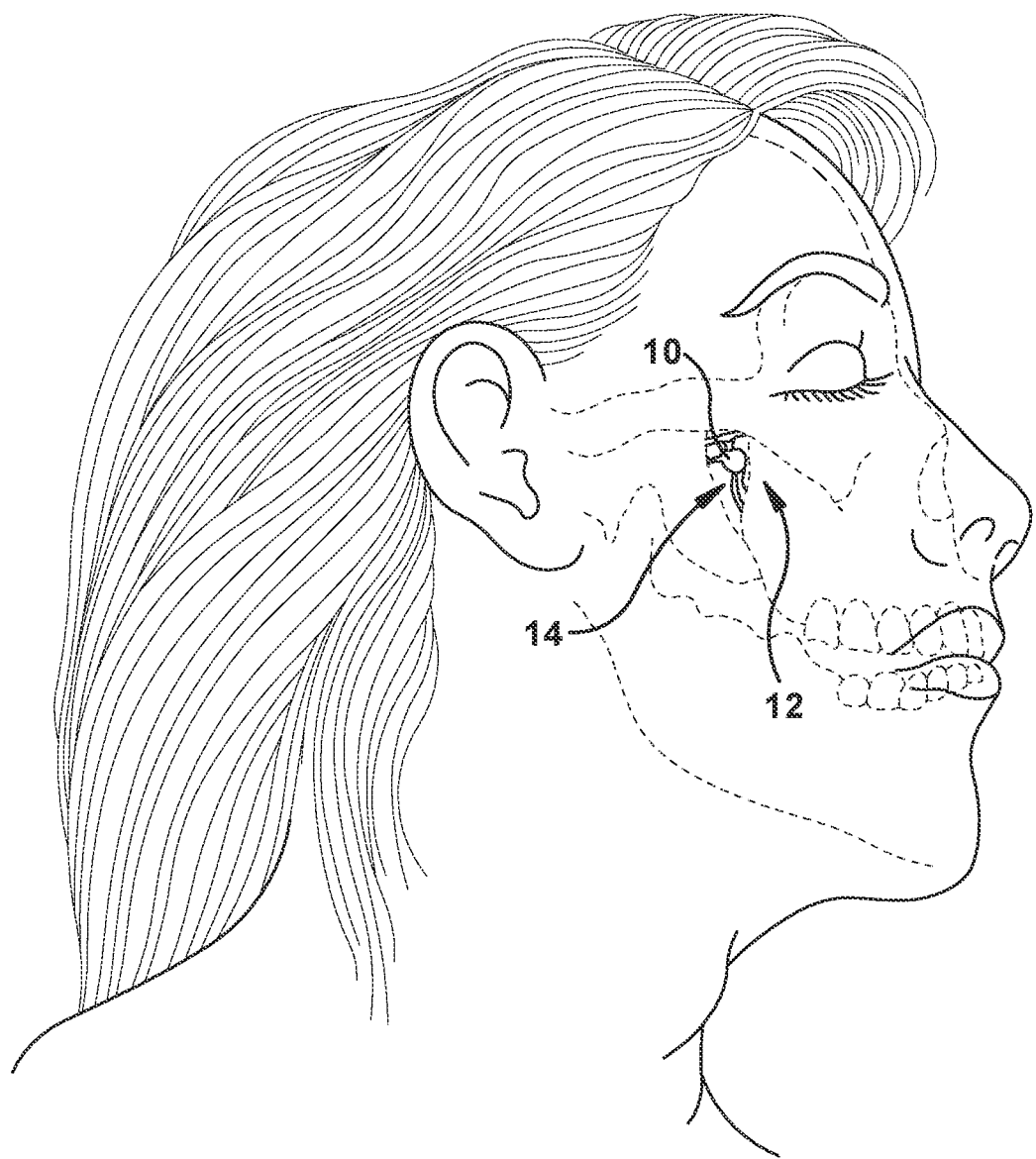
FIG. 1 is a perspective view showing part of the nervous innervation of the anterior craniofacial skeleton.

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the term "in communication" can refer to at least a portion of an electrode being adjacent, in the general vicinity, in close proximity, or directly next to and/or directly on (e.g., in physical contact with) a target neural structure, such as a sphenopalatine ganglion (SPG), a sphenopalatine nerve (SPN) (also called the "pterygopalatine nerve"), a vidian nerve (VN) (also called "the nerve of the pterygoid canal"), a greater petrosal nerve (GPN), a lesser petrosal nerve, a deep petrosal nerve (DPN), or a branch thereof (e.g., a nasopalatine nerve, a greater palatine nerve, a lesser palatine nerve, or a superior maxillary nerve). In some instances, the term can mean that at least a portion of an electrode is "in communication" with a target neural structure if application of a therapy signal (e.g., an electrical signal) thereto results in a modulation of neuronal activity to elicit a desired response, such as modulation of a nerve signal (e.g., an action potential or electrical impulse) generated in, or transmitted through, the target neural structure. In such instances, it can be understood that the electrode (or a portion thereof) is in electrical communication with the target neural structure.

An "SPG target site" includes a SPG, and afferent, efferent, parasympathetic, and sympathetic fibers that input and output the SPG. Non-limiting examples include the SPG, maxillary nerve, DPN, GPN, VN, nasopalatine nerve, superior posterior lateral nasal branches from the SPG, lesser palatine nerve, greater palatine nerve, and/or an inferior posterior lateral nasal branch from the greater palatine nerve. As used herein with respect to an SPG target site, the term "electrical communication" refers to the ability of an electric field generated by an electrode to be transferred to the SPG target site and/or to have a neuromodulatory effect on the SPG target site. The electrode can be positioned in direct electrical communication with the SPG such that electrode is adjacent to the SPG to directly stimulate the SPG. Such direct electrical stimulation is in contrast to an electrode being placed adjacent to a site distal or proximal to the SPG and thus directly stimulating such distal or proximal sites and indirectly stimulating the SPG. For example, placing an electrode in direct electrical communication with an SPG means that the electrode is not placed adjacent to distal or proximal sites that do or do not innervate the SPG such as, for example, the trigeminal nerve, a branch of the trigeminal nerve, a trigeminal ganglion or the vagus nerve.

As used herein, the term "electrical communication" with respect to a neurostimulator can refer to the ability of an electric field generated by an electrode or electrode array to be transferred, and/or to have a neuromodulatory effect, within and/or on a nerve, neuron, or fiber of a target neural structure.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, etc.

As used herein, the terms "modulate" or "modulating" with reference to activity of a target neural structure can refer to causing a change in neuronal activity, chemistry and/or metabolism. The change can refer to an increase, decrease, or even a change in a pattern of neuronal activity. The terms may refer to either excitatory or inhibitory stimulation, or a combination thereof, and may be at least electrical, magnetic, optical or chemical, or a combination of two or more of these. The terms "modulate" or "modulating"

can also be used to refer to a masking, altering, overriding, or restoring of neuronal activity.

As used herein, the terms "substantially blocked" or "substantially block" when used with reference to activity of a target neural structure can refer to a complete (e.g., 100%) or partial inhibition (e.g., less than 100%, such as about 90%, about 80%, about 70%, about 60%, or less than about 50%) of nerve conduction therethrough. For example, the terms "block", "blocking", and "blockade" can refer to the disruption, modulation, and/or inhibition of nerve impulse transmissions through a target neural structure.

As used herein, the term "activity" when used with reference to a target neural structure can, in some instances, refer to the ability of a nerve, neuron, or fiber to conduct, propagate, and/or generate an action potential. In other instances, the term can refer to the frequency at which a nerve or neuron is conducting, propagating, and/or generating one or more action potentials at a given moment in time. In further instances, the term can refer to the frequency at which a nerve or neuron is conducting, propagating, and/or generating one or more action potentials over a given period of time (e.g., seconds, minutes, hours, days, etc.).

As used herein, the terms "prevent" or "preventing" when used with reference to a medical condition (e.g., pain or headache) can refer to stopping a medical condition from occurring, or taking advance measures against the possibility or probability that a medical condition will happen or occur. In some instances, the terms can refer to an action or actions taken to decrease the chance that a subject will contract, develop, or suffer from a medical condition.

As used herein, the terms "suppress" or "suppressing" when used with reference to a medical condition can refer to refer to any quantitatively or qualitatively measurable or observable reduction or attenuation in a medical condition (e.g., a sign or symptom associated with the medical condition).

As used herein, the term "medical condition" can refer to any condition, state, or disease that is characterized, at least in part, by a disruption in sensory signals passing through or associated with the autonomic nervous system (ANS). Non-limiting examples of medical conditions can include pain, autonomic disorders, and neurological disorders. Other examples of medical conditions treatable by the present disclosure can include those disclosed in U.S. Pat. No. 6,526,318 to Ansarinia, U.S. Pat. No. 9,220,524 to Boling et al., U.S. patent application Ser. No. 13/746,038 to Caparso, U.S. patent application Ser. No. 13/917,917 to Goodman et al., U.S. patent application Ser. No. 13/917,953 to Goodman et al., and U.S. patent application Ser. No. 14/093,094 to Pless et al. For example, medical conditions can include headache pain. Headache pain can result from migraine headaches, including migraine headaches with aura, migraine headaches without aura, menstrual migraines, migraine variants, atypical migraines, complicated migraines, hem iplegic migraines, transformed migraines, and chronic daily migraines; episodic tension headaches; chronic tension headaches; analgesic rebound headaches; episodic cluster headaches; chronic cluster headaches; cluster variants; chronic paroxysmal hemicrania; hemicrania continua; post-traumatic headache; post-traumatic neck pain; post-herpetic neuralgia involving the head or face; pain from spine fracture secondary to osteoporosis; arthritis pain in the spine, headache related to cerebrovascular disease and stroke; headache due to vascular disorder; reflex sympathetic dystrophy, cervicalgia (which may be due to various causes, including, but not limited to, muscular, discogenic, or degenerative, including arthritic, posturally related, or metastatic); glossodynia, carotidynia; cricoidynia; otalgia due to middle ear lesion; gastric pain; sciatica; maxillary neuralgia; laryngeal pain, myalgia of neck muscles; trigeminal neuralgia (sometimes also termed tic douloureux); post-lumbar puncture headache; low cerebro-spinal fluid pressure headache; temporomandibular joint disorder; atypical facial pain; ciliary neuralgia; paratrigeminal neuralgia (sometimes also termed Raeder's syndrome); petrosal neuralgia; Eagle's syndrome; idiopathic intracranial hypertension; orofacial pain; myofascial pain syndrome involving the head, neck, and shoulder; chronic migraneous neuralgia, cervical headache; paratrigeminal paralysis; sphenopalatine ganglion neuralgia (sometimes also termed lower-half headache, lower facial neuralgia syndrome, Sluder's neuralgia, and Sluder's syndrome); carotidynia; Vidian neuralgia; and causalgia; or a combination of the above As used herein, the term "medical condition mediated by autonomic or neurological dysfunction" can refer to any condition, state, or disease that is characterized, at least in part, by a disruption in nerve signals (e.g., action potentials or electrical impulses) passing through or associated with the autonomic nervous system (ANS). Such medical conditions can result from, be caused by (e.g., directly or indirectly), or otherwise be associated with autonomic or neurological dysfunction. Non-limiting examples of medical conditions mediated by autonomic or neurological dysfunction are provided below.

As used herein, the terms "treat" or "treating" can refer to therapeutically regulating, preventing, improving, alleviating the symptoms of, and/or reducing the effects of a medical condition (e.g., mediated by autonomic or neurological dysfunction). As such, treatment also includes situations where a medical condition, or at least symptoms associated therewith, is completely inhibited, e.g., prevented from happening or stopped (e.g., terminated) such that the subject no longer suffers from the medical condition, or at least the symptom(s) that characterize the medical condition.

Overview

A brief discussion of the pertinent neurophysiology is provided to assist the reader with understanding certain aspects of the present disclosure.

The autonomic nervous system innervates numerous pathways within the human body and consists of two divisions: the sympathetic and the parasympathetic nervous systems. The sympathetic and parasympathetic nervous systems are antagonistic in their action, balancing the other system's effects within the body. The sympathetic nervous system (SNS) usually initiates activity within the body, preparing the body for action, while the parasympathetic nervous system (PNS) primarily counteracts the effects of the SNS.

The sphenopalatine ganglia 10 (FIG. 1) are located on both sides of the head. It shall be assumed for the following discussion of the present disclosure that reference is being made to the SPG 10 located on the left side of the head. The SPG 10 is located behind the posterior maxilla 12 in the PPF 14, posterior to the middle nasal turbinate (not shown in detail). The PPF is a small inverted pyramidal space measuring approximately 2 centimeters (cm) high and 1 cm wide and the SPG is approximately 4-5 millimeters (mm) in size. The SPG 10 is part of the parasympathetic division of the autonomic nervous system; however, the SPG has both sympathetic and parasympathetic nerve fibers, as well as sensory and motor nerve fibers either synapsing within the ganglion (e.g., parasympathetic) or fibers that are passing through the ganglion and not synapsing (e.g., sympathetic, sensory and motor).

The parasympathetic activity of the SPG 10 is mediated through the greater petrosal nerve (not shown), while the sympathetic activity of the SPG is mediated through the deep petrosal nerve (not shown), which is essentially an extension of the cervical sympathetic chain (not shown). Sensory sensations generated by or transmitted through the SPG 10 include, but are not limited to, sensations to the upper teeth, feelings of foreign bodies in the throat, and persistent itching of the ear. The SPG 10 transmits sensory information, including pain, to the trigeminal system via the maxillary division and ophthalmic division (not shown).

The present disclosure relates generally to neuromodulatory methods, and more particularly to methods for treating medical conditions by stimulation of a target neural structure. As discussed in more detail below, the present disclosure provides methods for suppressing or preventing medical conditions by disrupting sensory signals passing through the ANS, such as pain signals. The abnormal regulation of pain or autonomic pathways, which may be a feature of the medical conditions disclosed herein, can cause excitation, loss of inhibition, suppression, or loss of excitation of these pathways. Thus, in some instances, the present disclosure provides methods for applying one or more electrical signals to a target neural structure to modulate the transmission of sensory signals and stimulate or block the autonomic pathways passing through the target neural structure to reduce or eliminate one or more symptoms or signs associated with a medical condition. Similarly, application of one or more electrical signals to a target neural structure can modulate the transmission of sensory signals other than pain responsible for provoking or aggravating other undesirable sensations or conditions, such as nausea, bladder disorders, sleep disorders or abnormal metabolic states.

Systems

Figure 2:
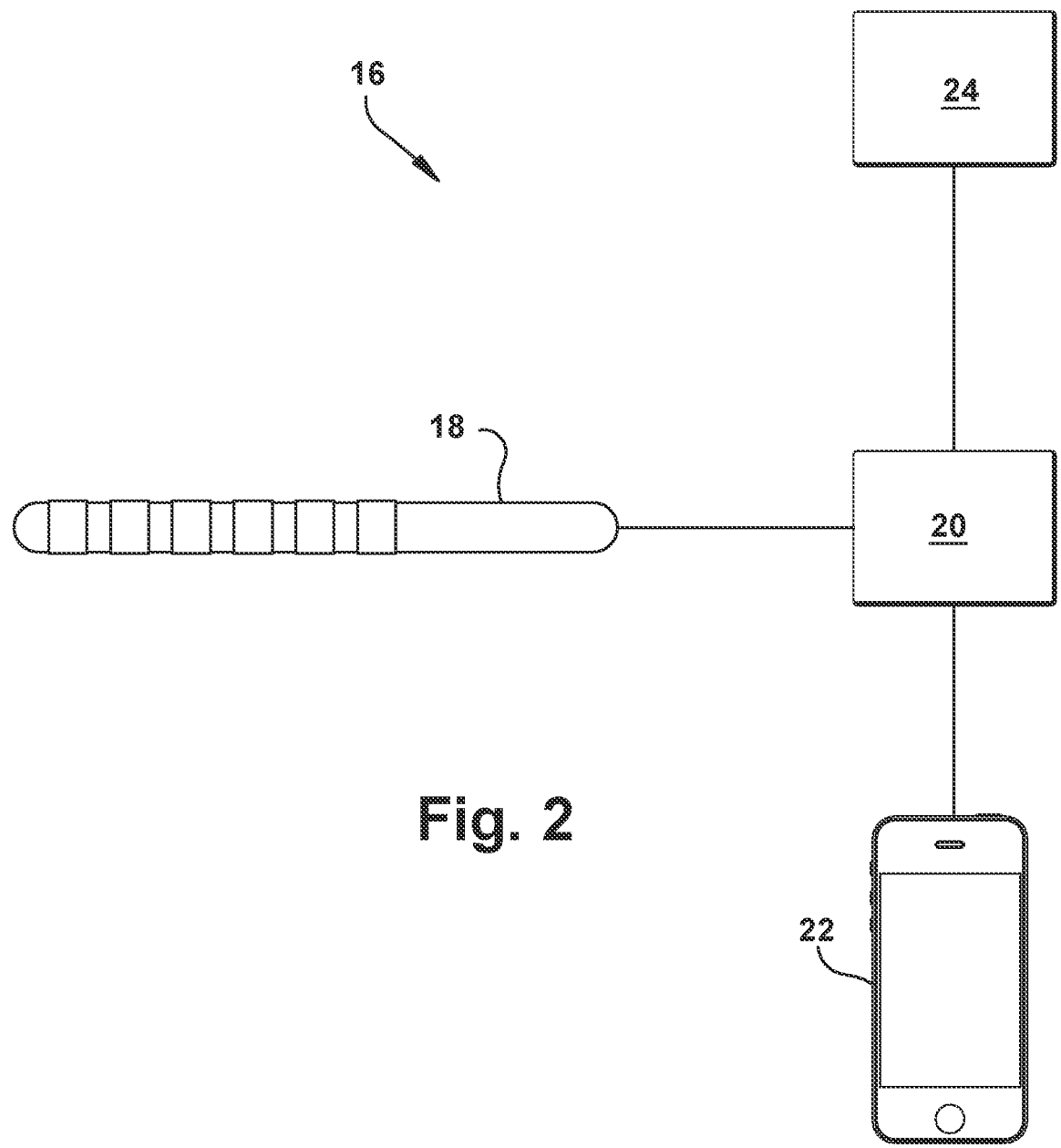
FIG. 2 is a schematic illustration showing a system for treating a medical condition in a patient constructed in accordance with one aspect of the present disclosure.

One aspect of the present disclosure can include a system 16 (FIG. 2) for preventing, suppressing, or treating a medical condition in a patient. The components of the system 16 can generally include a neurostimulator 18, a remote transducer 20, a personal electronic device 22 and, optionally, a programming device 24. As discussed below, each component of the system 16 can be in communication (e.g., electrical communication) with one another. In some instances, two or more components of the system 16 can be in wireless communication with one another. In other instances, two or more components of the system 16 can be in wired communication with one another. It will be appreciated that some components of the system 16 can be in wireless communication with one another while other components are in wired communication with one another.

In another aspect, the neurostimulator 18 can be sized and dimensioned for injection or insertion into a PPF 14 of a patient. The neurostimulator 18 can comprise electronic circuitry (not shown), one or more electrodes (not shown) that is/are driven by the circuitry, and one or more transmit coils, radiators, or PCB antennas (not shown). The electronic circuitry of the neurostimulator is programmed to receive and transmit data (e.g., stimulation parameters) and/or power from outside the body. In some instances, the electronic circuitry can be encapsulated by an insulative, biocompatible resin. The neurostimulator 18 can be entirely or partly formed from a flexible, biocompatible polymer. In some instances, the electronic circuitry can include a programmable memory for storing at least one set of stimulation and control parameters. In other instances, the neurostimulator 18 can include a power source (not shown) and/or power storage device (not shown). Possible power options can include, but are not limited to, various wireless charging mechanisms, such as an external power source coupled to the neurostimulator via an RF link using coils or radiators, a self-contained power source utilizing any means of generation or storage of energy (e.g., a primary battery, a rechargeable battery, such as a lithium ion battery, a button or coin cell battery, an electrolytic capacitor, or a super- or ultra-capacitor), and, if the self-contained power source is rechargeable, a mechanism for recharging the power source (e.g., an RF link). In some instances, the system 16 can include a retractable power cable (not shown) that can be selectively connected to the power source and/or power storage device.

Figure 3A:
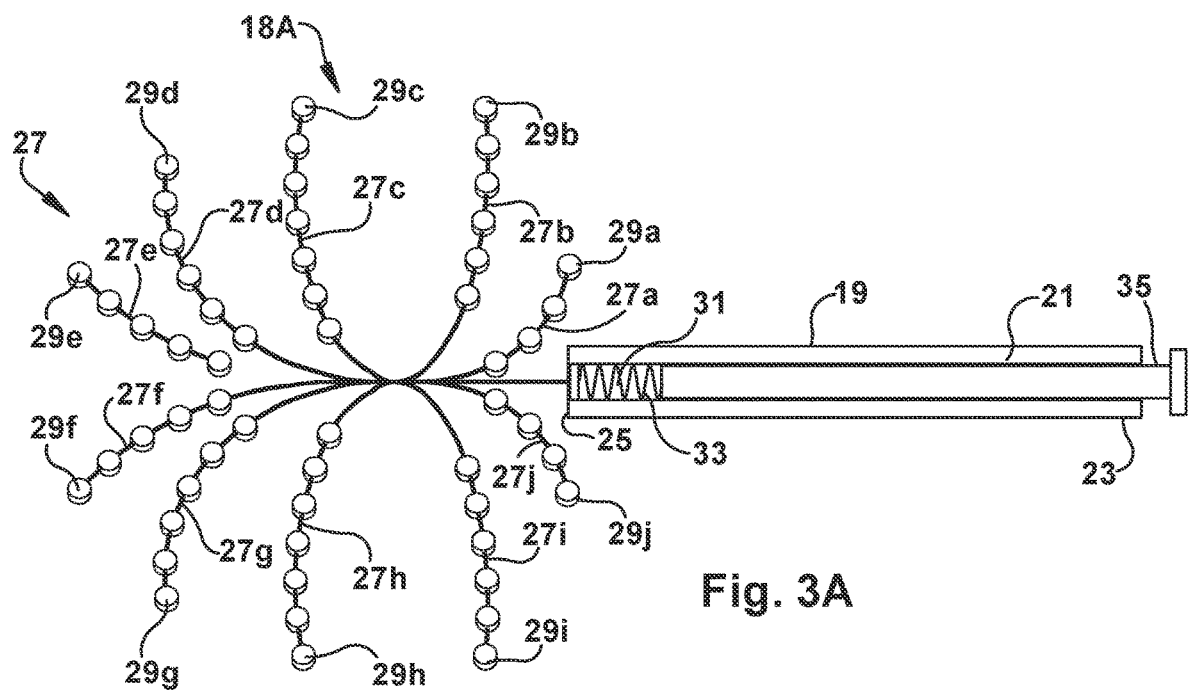
FIG. 3A is a partial cross-sectional view of a neurostimulator in accordance with an aspect of the present disclosure.

In certain embodiments, a neurostimulator 18 can comprise an electrode array or mesh that is expandable and deployable upon insertion at or near the target neural structure to fully or partially encapsulate or blanket the target neural structure. The electrode array or mesh can also comprise independently selectable electrical contacts. For example, referring to FIG. 3A, a system for treating a medical condition in a patient can include a sheath 19 having an inner lumen 21 with a proximal end 23 and a distal end 25. The system can further include a neurostimulator 18A sized and dimensioned for injection or insertion into the pterygopalatine fossa (PPF) of a patient. Neurostimulator 18A can comprise a neurostimulator electronics portion (not shown) and a plurality of expandable electrical leads 27 extending from the neurostimulator electronics portion. Each of the expandable electrical leads 27 can comprise a plurality of independently selectable electrical contacts 29. The neurostimulator electronics portion can include the electronic circuitry that drives the electrical contacts 29 and can be a separate component from the plurality of expandable electrical leads that is delivered after delivery of the plurality of expandable electrical leads and then connected to the plurality of expandable electrical leads. The plurality of expandable electrical leads 27 are disposed within sheath's inner lumen 21 in a non-deployed configuration and splay radially outward from distal end 25 of sheath's inner lumen 21 in a deployed configuration. FIG. 3A illustrates neurostimulator 18A in a deployed configuration. In a deployed configuration, the plurality of expandable electrical leads 27 are sized and dimensioned to partially or fully encapsulate or blanket a target neural structure in the PPF such as the SPG.

The plurality of electrical leads can be deployed from the sheath in a variety of ways. For example, the electrical leads can be spring-loaded as illustrated in FIG. 3A. In particular, the plurality of expandable electrical leads 27 can have a proximal end or base 31 that is in operable communication with a spring 33. The system can further include a trigger rod 35 that is slidably extendable through inner lumen 21 of sheath 19 and longitudinally aligned with spring 33. During insertion, the plurality of electrical leads 27 can be disposed within sheath 19. Upon reaching the target neural structure, such as a target SPG site, trigger rod 35 can be actuated by an operator to operably contact and compress spring 33 to urge the plurality of expandable electrical lead 27 radially outwards from distal end 25 of sheath 19. In such a deployed configuration, the plurality of expandable electrical leads can fully or partially encapsulate the target neural structure in the PPF such as the SPG. The electrical leads can be fabricated from a flexible material such that the electrical leads splay radially outwards upon deployment.

Figure 3B:
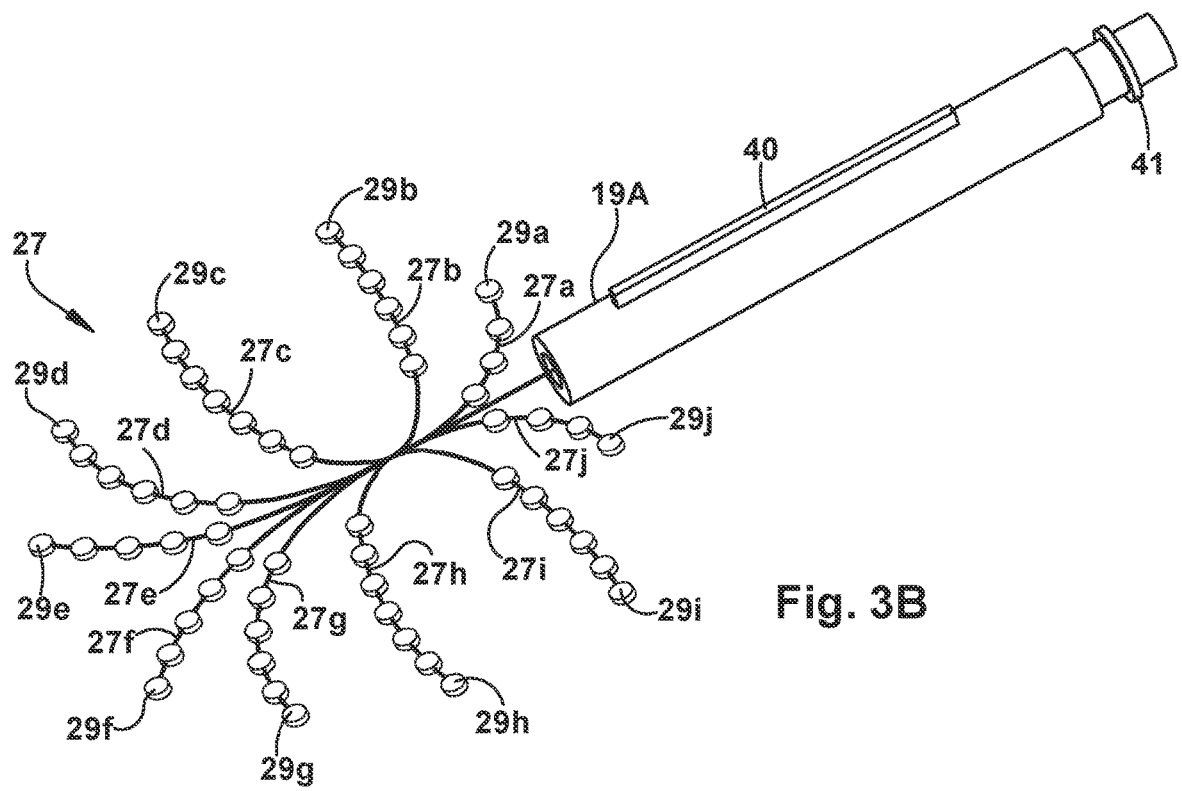
FIG. 3B is a perspective view of a neurostimulator in accordance with an aspect of the present disclosure.

Referring to FIG. 3B, in an alternative embodiment, a system can include a retractable sheath 19A and an insertion tool (not shown) that can be used to retract sheath 19A. The insertion tool can have a component configured to engage a complimentary component of the retractable sheath to retract the sheath when the neurostimulator is prepared to assume a deployed configuration. In the embodiment illustrated in FIG. 3B, the retractable sheath 19A can have a ridge 40 that engages a channel of the insertion tool but any other type of releasable mating mechanism can be used. During insertion, the plurality of electrical leads 27 is disposed within sheath 19A. Upon reaching the target neural structure, such as a target SPG site, the groove of the insertion tool can engage the ridge 40 of the retractable sheath 19A and be withdrawn proximally. This can retract sheath 19A to a soft stop 41, thereby exposing the plurality of expandable electrode leads 27. In such a deployed configuration, the plurality of expandable electrical leads can fully or partially encapsulate the target neural structure.

The plurality of expandable electrical leads can be partially or fully fabricated from a flexible and/or self-expanding material, such as nitinol.

Even though inserting a cylindrical lead with electrodes disposed thereon is an easier surgical procedure and involves less device components and thus has a lower likelihood of mechanical failure, inserting an electrode array or mesh as described herein can provide advantages such as, for example, facilitating paresthesia mapping inter-operatively and post-operatively. For example, since the SPG itself is difficult to visualize inter-operatively, the final location of the electrodes of the neurostimulator following implant can be determined utilizing paresthesia mapping. During paresthesia mapping, varying combinations of electrodes can be selected and the effects can be recorded on a homunculus map to determine if certain areas of the body that receive efferent input from an SPG target site experience paresthesia. If such areas experience paresthesia, this can be an indication that the neurostimulator is properly positioned to therapeutically stimulate the SPG target site. Similarly, after implantation, paresthesia mapping can be used to ensure the stimulation parameters and electrode locations are ideal such that the neurostimulator is therapeutically stimulating the SPG target site to treat the medical condition. Because the electrode array is radially expandable, it can be deployed to fully or partially encapsulate or blanket the SPG target site to place more electrical contacts in electrical communication with the SPG target site. Further, the independently selectable electrodes of the electrode array allow for precise paresthesia mapping for ideal neurostimulator placement and to confirm maximum therapeutic effect.

Figure 4:
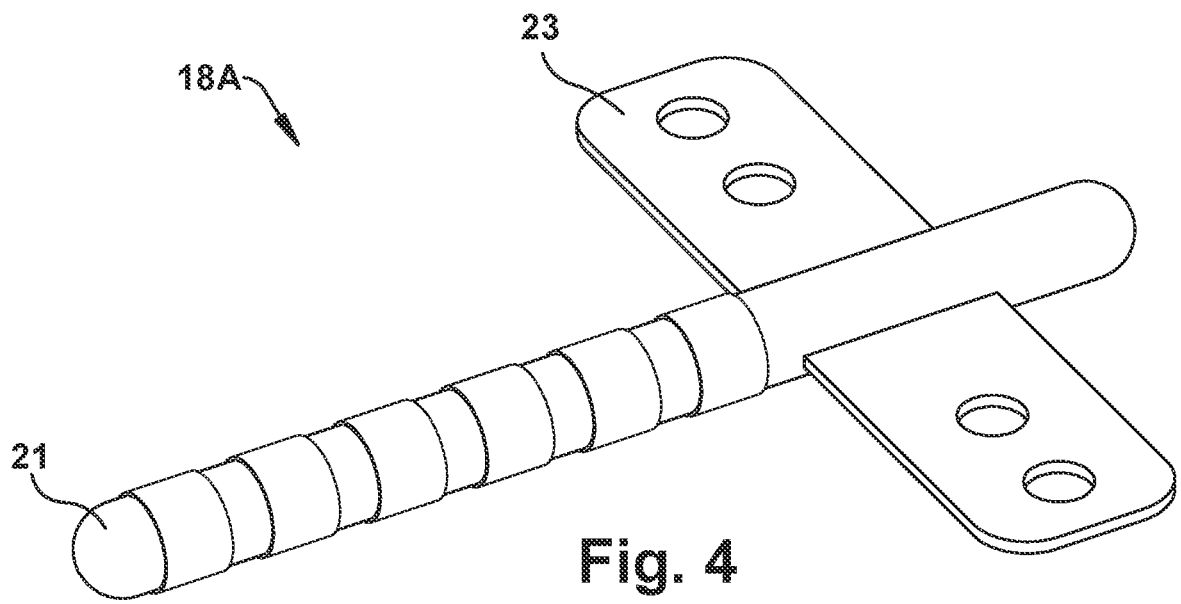
FIG. 4 is a perspective view of a neurostimulator in accordance with an aspect of the present disclosure.

Referring to FIG. 4, in certain embodiments, a neurostimulator 18A includes a neurostimulator body 21 and one or more tissue fixation devices, such as a suture tab(s) 23 molded or otherwise attached to neurostimulator body 21.

In some instances, the neurostimulator 18 can be sized and dimensioned for injection or insertion into the PPF 14 via an elongated, hollow delivery device 26 (FIGS. 4A-B) comprised, for example, of a stiff, dielectric material with sufficient lubricity to permit the undamaged passage of neurostimulator 18 (FIG. 2) therethrough. The delivery device 26 (FIGS. 6A-B) can comprise, for example, a hypodermic needle, a catheter, or a catheter-like device. In one example, the delivery device 26 can be configured to include a connection (not shown) within the delivery device (e.g., an electrical connection) with the neurostimulator 18 to allow stimulation and response profiling during implantation of the neurostimulator. In another example, the delivery device 26 can be configured to include a navigation tip (not shown) (e.g., at or near a proximal end thereof) to facilitate placement.

In another aspect, the system 16 can include a remote transducer 20 in electrical communication (e.g., wireless communication) with the neurostimulator 18. The remote transducer 20 can be programmed and configured for delivery of an electrical signal to the neurostimulator 18. In some instances, the remote transducer 20 can comprise a replaceable or rechargeable power source (not shown) and a transmit coil (not shown), each of which is partly or entirely located within a housing (not shown). The remote transducer 20 is adapted for placement on or about a patient's head, e.g., adjacent an implanted neurostimulator 18 of the present disclosure. For example, the remote transducer 20 can be configured as a patch, a wand, a headset or glasses. In such instances, the remote transducer 20 can be programmed to provide user feedback to assist the subject in optimizing placement of the transducer about the subject's body. Where the remote transducer 20 is configured as a patch, at least one skin-contacting surface of the patch can include an adhesive coating or other material (e.g., a hydrogel) to permit attachment of the patch to a skin surface (e.g., the cheek) of a patient. Additionally, where the remote transducer 20 is configured as a patch, the patch can be adapted to fit on replacement skin patches. The patch can also include such components as a rechargeable battery, Bluetooth capability, and closed-loop control circuits (described more below).

In another aspect, the system 16 can include a personal electronic device 22 that is in electrical communication (e.g., wireless communication) with the remote transducer 20. Examples of personal electronic devices 22 can include smart phones and tablets; although, it will be appreciated that personal computers (PCs) may also be included. In some instances, the personal electronic device 22 can include software programmed to control one or more stimulation and/or control parameters associated with the neurostimulator. Additionally, or optionally, the software comprising the personal electronic device 22 can be programmed to store patient therapy data, such as diary questions and patient incentive information, and/or promote patient-to-patient interaction. For instance, the personal electric device 22 can be programmed to include an electronic leader board where patients are ranked against other patients based on certain usage goals. The personal electronic device can also be programmed to interact with an incentive program for patients to earn "points" for compliance (e.g. activating the device once every day for 20 minutes) so that a manufacturer could study new therapies or gather product data. The personal electronic device 22 can also include software programmed to access remote data sources (e.g., Internet websites), query certain data, and then provide stimulation instructions to the system 16 based on the queried data. For example, the personal electronic device 22 can access a website that provides weather-related information (e.g., Accuweather) and then, based on information obtained from the website, provide predictive information and/or stimulation instructions for a particular medical condition (e.g., migraine). In another example, the personal electronic device 22 can also include software programmed to provide the neurostimulator 18 with customizable or patient-triggered alerts, e.g., indicating stimulation periods and the duration of each period, after a desired period of time (e.g., 1.5 hours) after sleep onset, or after consumption of food or water. In some instances, the personal electronic device 22 can be operated manually by the patient or a caregiver.

In another aspect, the system 16 can additionally or optionally comprise a programming device 24 that is in electrical communication (e.g., wireless communication) with the remote transducer 20. The programming device 24 can be configured and programmed to deliver stimulation and/or control instructions to the remote transducer 20. In one example, the programming device 24 can be configured as a dedicated, smart phone-sized unit. In another example, the programming device 24 can be configured as a smart phone accessory dongle. In some instances, the programming device 24 can be operated manually by the patient or a caregiver. In other instances, the programming device 24 can be battery powered and/or directly powered, e.g., by an AC source. If powered by rechargeable batteries, a battery charger may be an accessory to the programming device 24.

In another aspect, the system 16 can include one or more sensors (not shown) to permit open- or closed-loop control. In an open-loop system, for example, the system 16 can include one or more sensors such that a patient can manage (e.g., prophylactically) treatment of a medical condition based on feedback (e.g., detected signals) from the sensor(s). Such detected signals can be indicative of the onset of a medical condition, such as an increase in blood flow, skin resistance, temperature, etc. Upon noticing the signal(s), the patient can then trigger or activate the neurostimulator 18 to prevent or mitigate onset of the medical condition.

In another aspect, the system 16 can include one or more sensors to permit closed-loop control by, for example, automatically responding (e.g., by activation of the neurostimulator 18) in response to a sensed environmental parameter and/or a sensed physiological parameter, or a related symptom or sign, indicative of the extent and/or presence of a medical condition. In one example, the sensor(s) can detect an environmental parameter, such as barometric pressure, ambient temperature, humidity, etc. In another example, the sensor(s) can detect a physiological parameter, or a related symptom or sign, indicative of the extent and/or presence of a medical condition, non-limiting examples of which include skin resistance, blood flow, blood pressure, a chemical moiety, nerve activity (e.g., electrical activity), protein concentrations, electrochemical gradients, hormones (e.g., cortisol), electrolytes, markers of locomotor activity, and cardiac markers (e.g., EKG RR intervals). Sensors used as part of a closed- or open-loop system can be placed at any appropriate anatomical location on a subject, including a skin surface, an intra-oral cavity, a mucosal surface, or at a subcutaneous location. Examples of sensors and feedback control techniques that may be employed as part of the present disclosure are disclosed in U.S. Pat. No. 5,716,377.

Methods

Figure 5:
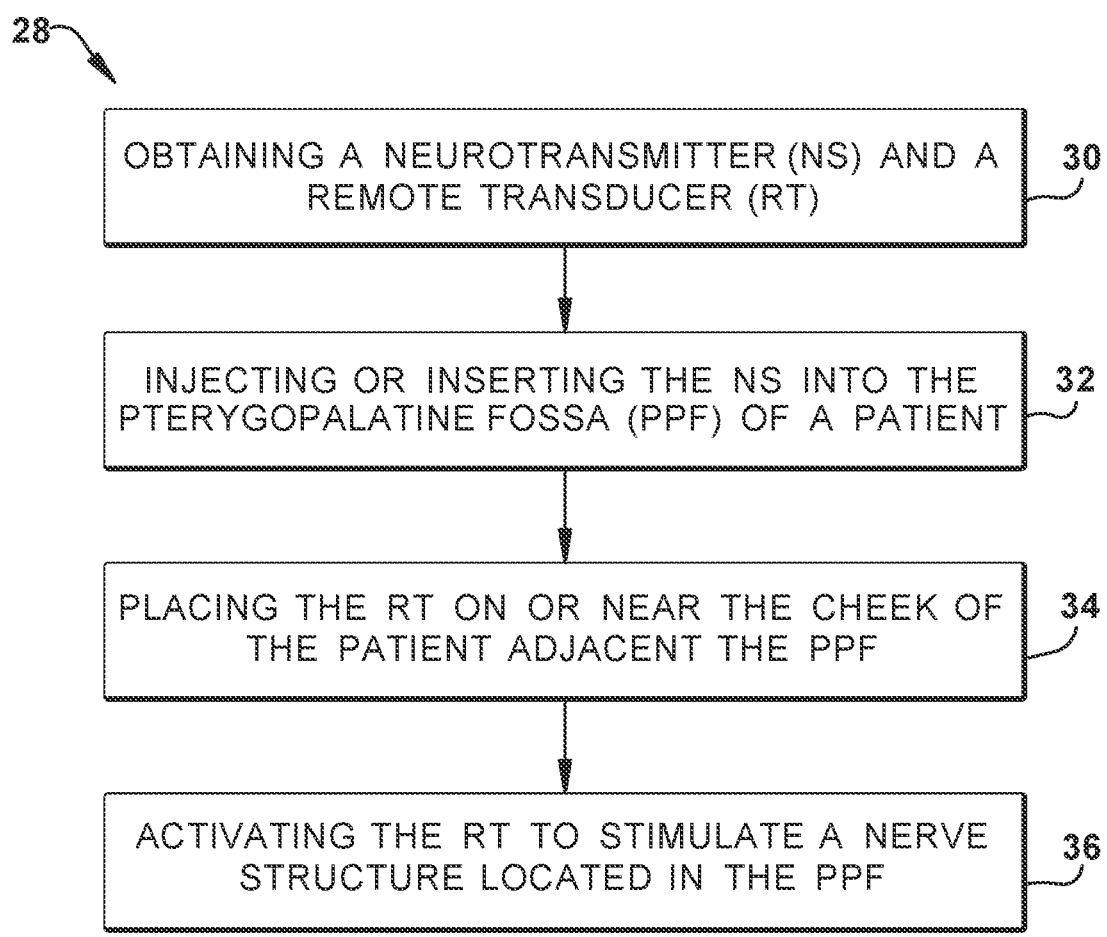
FIG. 5 is a process flow diagram illustrating a method for treating a medical condition in a patient according to another aspect of the present disclosure.

Another aspect of the present disclosure can include a method 28 (FIG. 5) for suppressing, preventing, or treating a medical condition in a patient. In some instances, the method 28 of the present disclosure can act to suppress or prevent the medical condition by disrupting nerve signals passing through the ANS as the signals traverse, or are generated in, the target neural structure. As shown in FIG. 3, the method 28 can generally include the following steps: obtaining a neurostimulator 18 and a remote transducer 20 (Step 30); injecting or inserting the neurostimulator into the PPF 14 of a patient (Step 32); placing the remote transducer on or near the cheek of the patient adjacent the PPF (Step 34); and activating the remote transducer to stimulate a target neural structure in the PPF (Step 36).

In certain embodiments, a method for treating a medical condition in a patient can comprise inserting or injecting a sheath into a PPF of the patient. The sheath can have an inner lumen with a proximal end and a distal end. Disposed within the sheath is a neurostimulator comprising a plurality of expandable electrical leads each comprising a plurality of independently selectable electrical contacts. The method can further include advancing the sheath to a target neural structure in the PPF. Once reaching the target neural structure, the plurality of expandable electrical leads can be deployed to splay outwards from the sheath and fully or partially encapsulate the target neural structure. The method can further comprises activating one or more of the plurality of independently selectable electrical contacts to deliver a therapeutic electrical signal to the target neural structure to treat the medical condition.

There are several surgical approaches to the PPF 14 that may be used to deliver a neurostimulator 18 into the PPF according to the present disclosure. One approach is a gingival-buccal approach, which is described in U.S. Pat. No. 9,211,133 to Papay and describes a therapy delivery device that has a curvilinear shape. Another approach is a trans-oral approach, with a dental needle up to the sphenopalatine foramen through the posterior palatine canal (see U.S. Pat. No. 8,229,571 to Benary et al.). Yet another approach is a lateral approach with a straight needle to the PPF 14 through the infratemporal fossa (see U.S. Pat. No. 6,526,318 to Ansarinia). A further approach includes an infrazygomatic approach, in which the skin entry is at a site overlying the PPF 14, just inferior to the zygoma and anterior to the mandible. Other routes through the mouth and outer skin of the face are described in M. duPlessis et al., *Clinical Anatomy* 23 (8, 2010):931-935, Micah Hill et al., *Operative Techniques in Otolaryngology* 21 (2010):117-121, and MI Syed et al., *Radiology of Non-Spinal Pain Procedures. A Guide for the Interventionist*. Chapter 2. Head and Neck. pp. 5-42 (Heidelberg: Springer, 2011).

One example of the method 28 is illustrated in FIGS. 6A-7B, whereby a lateral approach to the PPF 14 through the infratemporal fossa is shown. At Step 30, the method 28 can include providing a neurostimulator 18 and a remote transducer 20. In some instances, the neurostimulator 18 and the remote transducer 20 can comprise a system 16 as described above. For example, the system 16 can include the neurostimulator 18, the remote transducer 20, a personal electronic device 22, and a programming device 24.

At Step 32, the neurostimulator 18 can be injected or inserted into the PPF 14 of the patient. A delivery device 26 for introducing the neurostimulator 18 can be used to implant the neurostimulator in the PPF 14 on or proximate to a target neural structure, such as the SPG 10. For example, the delivery device 26 can include a needle, such as a 12-gauge, 14-gauge, 16-gauge, 18-gauge, or 20-gauge needle, depending upon the diameter of the neurostimulator 18 to be implanted. Next, the SPG 10 can be localized using at least one scanning apparatus, such as a CT scan or fluoroscope. Further details of the localization procedure are disclosed in U.S. Pat. No. 6,526,318 to Ansarinia.

The entry point for the insertion of the delivery device 26 can be located in the coronoid notch between the condylar and coronoid processes of the ramus of the mandible. Once the entry point is localized, the skin overlying the entry point can be shaved and prepared with antiseptic solution. A 25-gauge needle can be used to inject a subcutaneous local anesthetic (e.g., 2 cc of 2% lidocaine) into the skin and subcutaneous tissues overlying the entry point. In addition to the local anesthetic, the patient may be given intravenous sedation and prophylactic antibiotics prior to commencement of the implantation procedure, if desired.

Figure 6A:
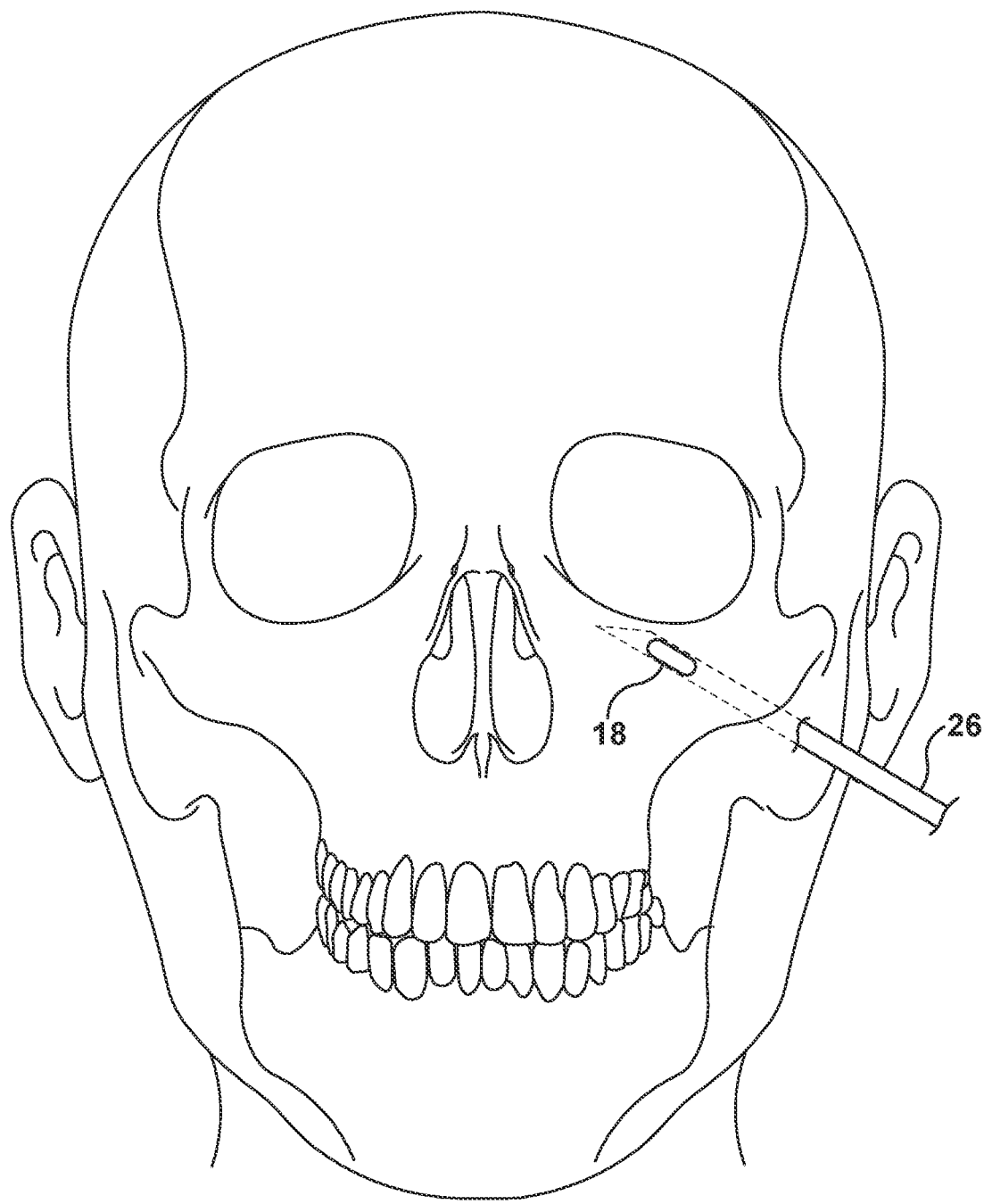
FIGS. 6A-B are schematic illustrations showing a neurostimulator being delivered into a pterygopalatine fossa (PPF) of a patient according to another aspect of the present disclosure.
Figure 6B:
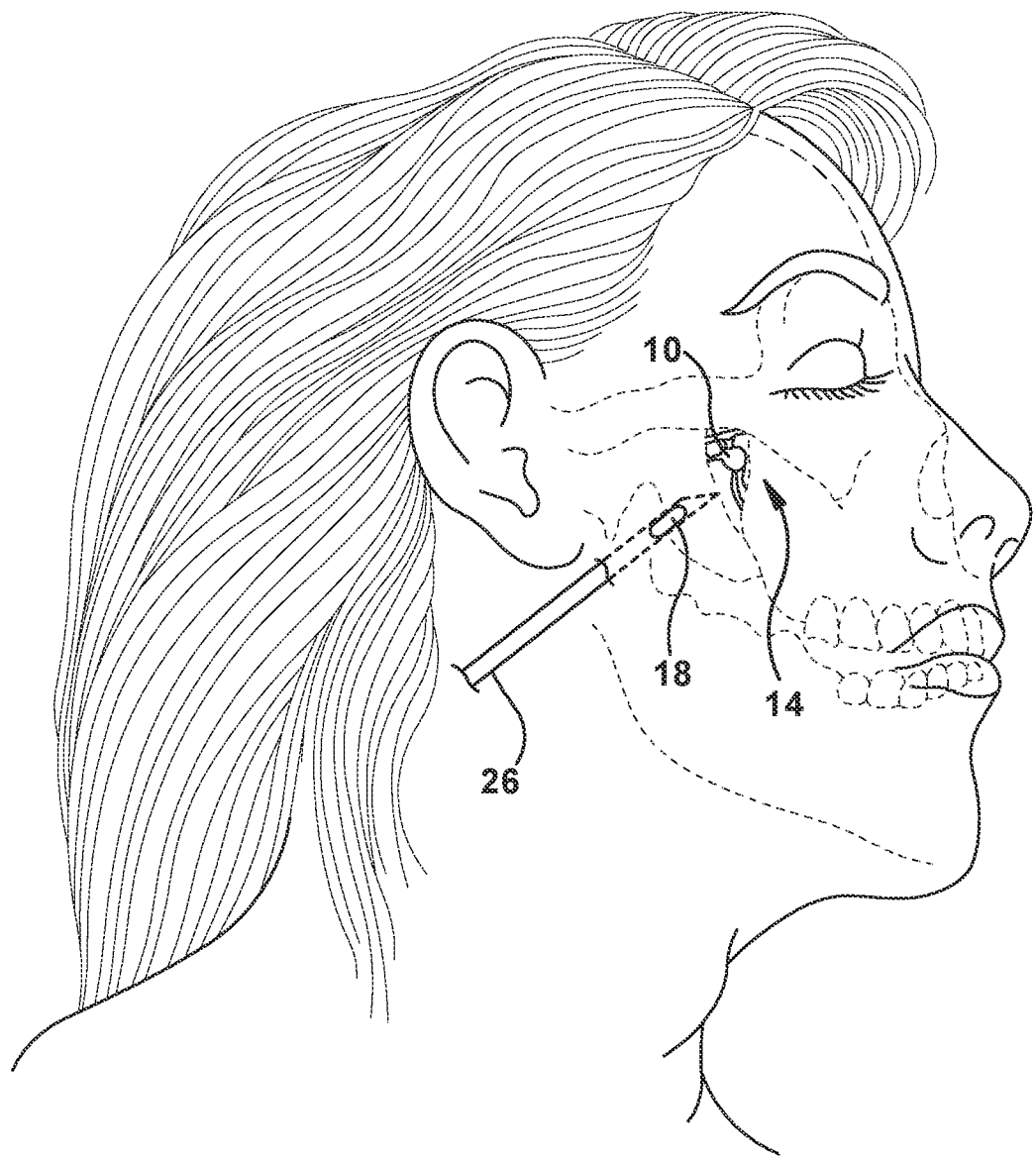

The delivery device 26 can be inserted at the entry point and advanced between the coronoid process and the condylar process of the ramus of the mandible towards the PPF 14 (FIGS. 6A-B). The delivery device 26 can be slowly advanced in the medial fashion perpendicular to the skin in the anterior-posterior (transverse) plane along the direction of the x-ray beam of the fluoroscope until it enters the PPF 14. Once the delivery device 26 is positioned according to whether implantation is desired on or adjacent the SPG 10, a stylet (not shown) is withdrawn from the delivery device 26. An electrode (not shown) can then be placed within the central channel of the delivery device 26 and used to test the placement of the delivery device. Next, the neurostimulator 18 can be advanced to the distal tip of the delivery device 26 to place the neurostimulator on or proximate to the target neural structure (e.g., the SPG 10).

In one example, the neurostimulator 18 can be implanted in the patient without penetrating the cranium of the patient.

In another example, the neurostimulator 18 can be implanted in the patient without penetrating the palate and/or without entering the nasal cavity of the patient.

At Step 34, the remote transducer 20 can be brought into contact (or close contact) with the head of the patient so that the remote transducer is within close proximity (approximately 2 centimeters to approximately 10 meters) to the implanted neurostimulator 18. Where the remote transducer 20 comprises a patch, for example, a skin-contacting surface of the patch can be brought into direct contact with the cheek of the patient, immediately adjacent the location of the implanted neurostimulator 18.

Figure 7A:
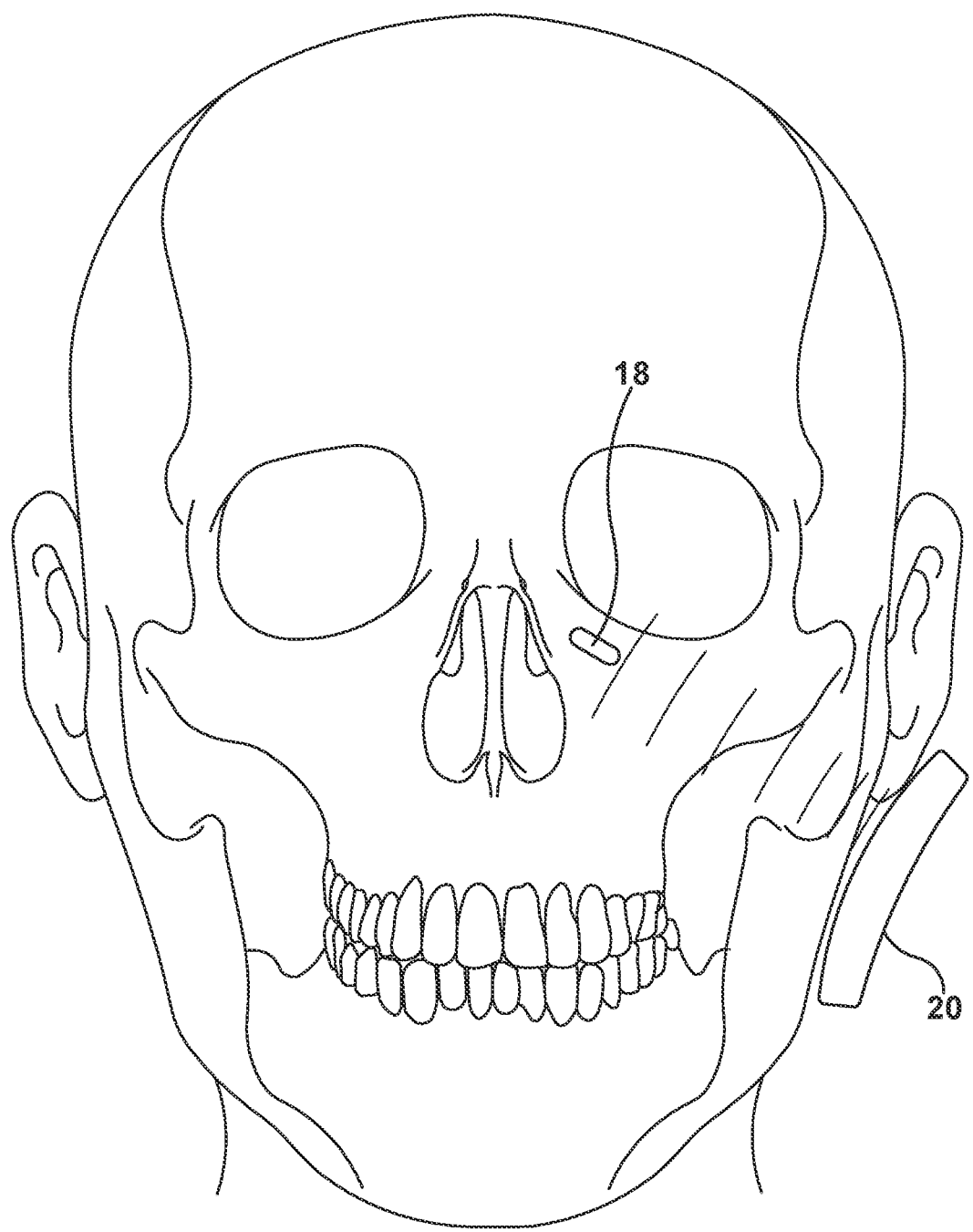
FIGS. 7A-B are schematic illustrations showing the neurostimulator in FIGS. 6A-B implanted in the PPF and receiving an electrical signal from a remote transducer to treat a medical condition in the subject.
Figure 7B:
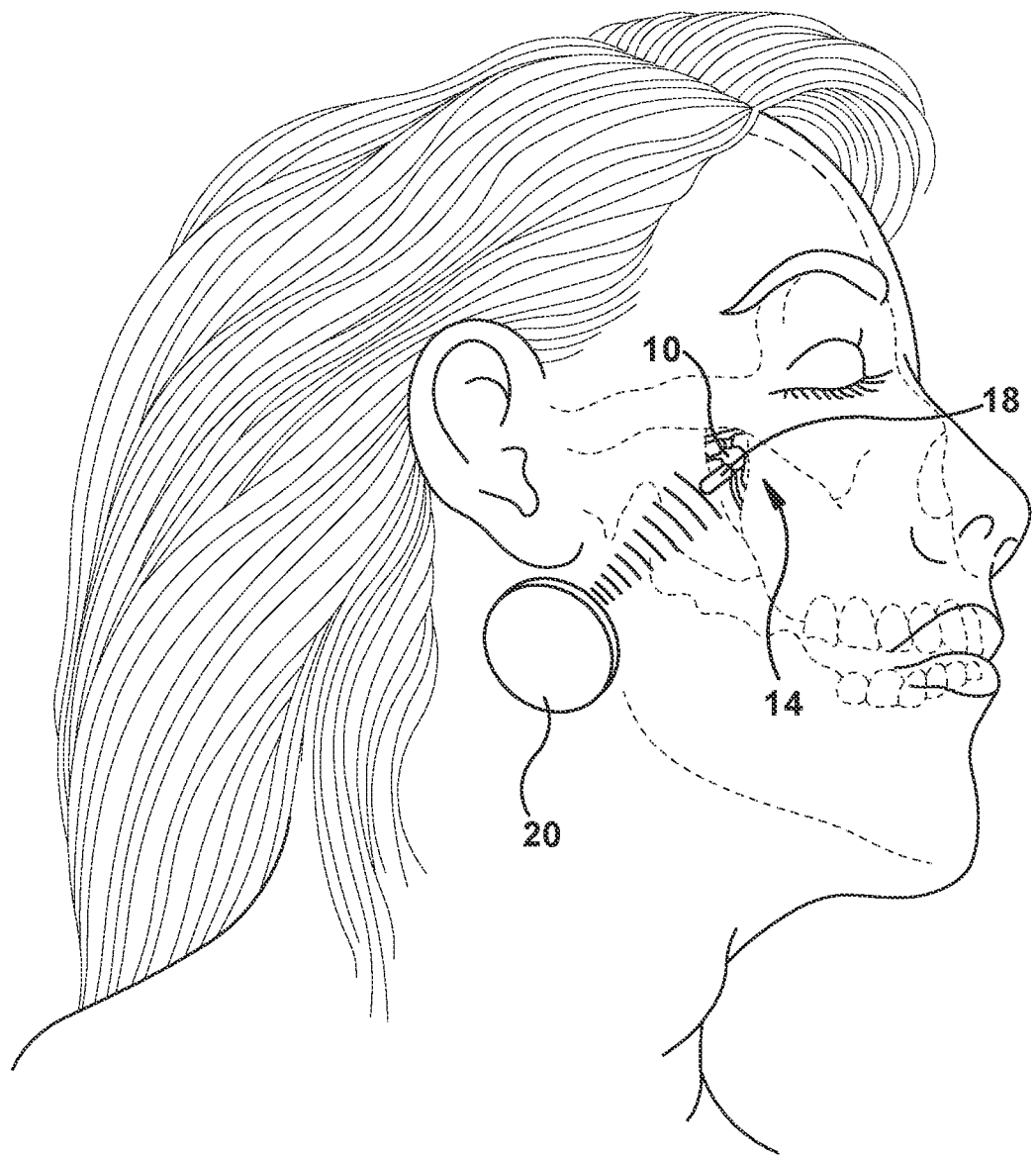

At Step 36, the remote transducer 20 can be activated (FIGS. 7A-7B). Activation of the remote transducer 20 causes the neurostimulator 18 to deliver an electrical signal to the target neural structure (e.g., the SPG 10). In some instances, electrical energy can be applied to the target neural structure (e.g., the SPG 10) for a time and in an amount insufficient to cause a lesion on the target neural structure. In other instances, electrical energy can be delivered to the target neural structure in any of several forms, such as biphasic charge-balanced pulses having a frequency of about 1-1000 Hz (e.g., 5-200 Hz), a pulse-width of about 0.04-2 ms, a current of about 0.05-100 mA (e.g., 0.1-5 mA), and a voltage of about 1-10 V. In addition, electrical modulation can be controllable such that either anodic or cathodic stimulation may be applied. Electrical energy may be delivered continuously, intermittently, as a burst in response to a control signal, or as a burst in response to a sensed parameters, such as increased SPG 10 neural activity. The electrical parameters may also be adjusted automatically based on a control signal, based on sensed parameters, or by selection by the patient (e.g., using the personal electronic device). The electrical energy can be applied to the target neural structure for a time and in an amount sufficient to treat the medical condition.

From the above description of the present disclosure, those skilled in the art will perceive improvements, changes and modifications. For example, it will be appreciated that the method 28 of the present disclosure can be performed to modulate activity of a target neural structure on either or both sides of a patient's head. Such improvements, changes, and modifications are within the skill of those in the art and are intended to be covered by the appended claims. All patents, patent applications, and publication cited herein are incorporated by reference in their entirety.

The following is claimed:

1. A medical system for treating a medical condition in a patient comprising:
   a neuro device configured to be implanted in a head of a patient, the neuro device including
      a plurality of expandable electrical leads each comprising a plurality of electrical contacts, wherein the expandable electrical leads are configured to be in communication with a neural structure of the skull of the patient when the neuro device is implanted in the head of the patient, wherein the expandable electrical leads are configured to encapsulate the neural structure,
      electronic circuitry in communication with the plurality of the expandable electrical leads, the electronic circuitry being encapsulated,
      a power source for operating the neuro device, the power source being configured to be wirelessly rechargeable; and
   one of a smart phone and a smart tablet in wireless communication with the electronic circuitry of the neuro device.

2. A method of treating a medical condition of a patient comprising:
   inserting a neuro device into a head of the patient such at least one expandable electrical lead of the neuro device is in communication with a neural structure of the head of the patient, wherein at least one the expandable electrical lead is in a non-deployed configuration during inserting the neuro device into the head of the patient, wherein the at least one expandable electrical lead includes a plurality of electrical contacts, wherein the at least one expandable electrical lead encapsulates the neural structure; and
   wirelessly connecting the neuro device to one of a smart phone and a smart tablet such that the neuro device and said at least one of a smart device and a smart tablet are in communication with one another.

3. A method of treating a medical condition of a patient comprising:
   inserting a plurality of expandable electrical leads through a sheath of a delivery device and into head of the patient such that the plurality of expandable electrical leads are in communication with a neural structure of the head of the patient, wherein the plurality of expandable electrical leads are in a non-deployed configuration during inserting the plurality of expandable electrical leads through the sheath, wherein the at least one electrical lead includes a plurality of electrical contacts, wherein the at least one expandable electrical lead encapsulates the neural structure; and
   wirelessly connecting the plurality of expandable electrical leads to one of a smart phone and a smart tablet such that the plurality of expandable electrical leads and said at least one of a smart device and a smart tablet are in communication with one another.

4. The medical system of claim 1, wherein the plurality of expandable electrical leads are configured to splay radially outward in a deployed configuration.

5. The medical system of claim 1, wherein the plurality of expandable electrical leads are sized and dimensioned to at least partially blanket a target neural structure in the pterygopalatine fossa.

6. The medical system of claim 1, wherein the plurality of expandable electrical leads are sized and dimensioned to at least partially encapsulate a target neural structure in the pterygopalatine fossa.

7. The method of claim 2, further comprising deploying the at least one expandable electrical lead within the neural structure of the head of the patient.

8. The method of claim 3, further comprising deploying the plurality of expandable electrical leads into the head of the patient.

9. The method of claim 8, wherein deploying the plurality of expandable electrical leads into the head of the patient further comprises splaying the expandable electrical leads radially outwards from an inner lumen of the sheath.

\* \* \* \* \*